United States Patent
Ritter et al.

(10) Patent No.: US 11,660,162 B2
(45) Date of Patent: May 30, 2023

(54) ARTHROSCOPIC SHAVER AND CLEANING DEVICE AND METHOD OF CLEANING AN ARTHROSCOPIC SHAVER

(71) Applicant: Mark 2 Medical, LLC, Noblesville, IN (US)

(72) Inventors: Mark Ritter, Zionsville, IN (US); Mark Dale, Noblesville, IN (US)

(73) Assignee: Mark 2 Medical, LLC, Noblesville, IN (US)

( * ) Notice: Subject to any disclaimer, the term of this patent is extended or adjusted under 35 U.S.C. 154(b) by 0 days.

(21) Appl. No.: 15/844,265

(22) Filed: Dec. 15, 2017

(65) Prior Publication Data

US 2019/0183604 A1 Jun. 20, 2019

(51) Int. Cl.
*A61B 90/70* (2016.01)
*B08B 9/032* (2006.01)
*A61B 17/32* (2006.01)

(52) U.S. Cl.
CPC .......... *A61B 90/70* (2016.02); *B08B 9/0325* (2013.01); *A61B 17/32002* (2013.01); *A61B 17/320016* (2013.01); *B08B 2209/032* (2013.01)

(58) Field of Classification Search
CPC ...... A61B 17/320016; A61B 17/32002; A61B 90/70; B08B 2209/032; B08B 9/0325
See application file for complete search history.

(56) References Cited

U.S. PATENT DOCUMENTS

| | | | | |
|---|---|---|---|---|
| 4,897,079 A | * | 1/1990 | Zaleski | A61M 1/85 604/22 |
| 5,279,317 A | * | 1/1994 | Bowman | A61B 1/121 134/166 C |
| 5,511,568 A | | 4/1996 | Bowman et al. | |
| 5,511,598 A | | 4/1996 | Bowman et al. | |
| 5,947,990 A | * | 9/1999 | Smith | A61B 17/32002 606/180 |
| 6,004,509 A | * | 12/1999 | Dey | A61B 90/40 134/22.12 |
| 6,132,448 A | * | 10/2000 | Perez | A46B 5/0087 606/180 |
| 6,419,688 B1 | * | 7/2002 | Bacher | A61B 17/295 606/205 |

(Continued)

FOREIGN PATENT DOCUMENTS

WO 2013162699 A1 10/2013

OTHER PUBLICATIONS

PCT/US2018/062879, International Search Report, International Searching Authority, dated Jan. 31, 2019.

(Continued)

*Primary Examiner* — Christopher Remavege
(74) *Attorney, Agent, or Firm* — Ice Miller LLP

(57) ABSTRACT

An arthroscopic shaver cleaning device and method of cleaning an arthroscopic shaver blade/burr are disclosed. The arthroscopic shaver cleaning device includes a sleeve portion configured to interface with a proximal portion of a blade/burr of an arthroscopic shaver. The arthroscopic shaver cleaning device further includes a fluid connection portion having a fluid passageway configured to direct fluid toward the proximal portion of the blade/burr in order to dislodge debris entrapped in shaver lumen of the blade/burr.

12 Claims, 5 Drawing Sheets

(56) References Cited

U.S. PATENT DOCUMENTS

| | | | |
|---|---|---|---|
| 6,958,071 B2* | 10/2005 | Carusillo | A61B 17/32002 606/170 |
| 8,267,896 B2* | 9/2012 | Hartoumbekis | A61B 1/126 604/167.01 |
| 9,572,623 B2* | 2/2017 | Long | A61B 18/1477 |
| 10,383,700 B2* | 8/2019 | Blumenkranz | B08B 9/00 |
| 2005/0171487 A1 | 8/2005 | Haury et al. | |
| 2006/0025794 A1* | 2/2006 | Fanton | A61B 17/32002 606/170 |
| 2007/0181157 A1* | 8/2007 | Dadourian | B08B 9/0325 134/22.12 |
| 2009/0286030 A1* | 11/2009 | Robert | A61L 2/18 428/36.91 |
| 2011/0094599 A1* | 4/2011 | Meyer | B08B 9/032 137/15.04 |
| 2013/0133698 A1* | 5/2013 | Meyer | B08B 9/0321 134/22.11 |
| 2013/0267892 A1* | 10/2013 | Woolford | A61M 3/0258 604/34 |
| 2013/0306112 A1 | 10/2013 | Blumenkranz | |
| 2014/0025070 A1* | 1/2014 | Kerr | A61B 17/295 606/41 |
| 2014/0166054 A1* | 6/2014 | Moberg | B08B 9/0328 134/22.12 |
| 2014/0190523 A1* | 7/2014 | Garvey | A61B 90/70 134/22.12 |
| 2014/0352724 A1 | 12/2014 | Meyer | |
| 2015/0087911 A1* | 3/2015 | Konstorum | A61B 1/015 600/157 |
| 2016/0059280 A1* | 3/2016 | Prescott | B08B 9/0321 134/22.12 |
| 2016/0278876 A1* | 9/2016 | Garvey | A61B 90/70 |
| 2017/0239696 A1* | 8/2017 | Weber | A61B 17/00234 |
| 2019/0059925 A1* | 2/2019 | Smith | A61B 17/3203 |

OTHER PUBLICATIONS

PCT/US2018/062879, Written Opinion of the International Searching Authority, International Searching Authority, dated Jan. 31, 2019.

Extended European Search Report, Application No. 18889111.3, European Patent Office, dated Jul. 19, 2021.

* cited by examiner

ARTHROSCOPIC SHAVER AND CLEANING DEVICE AND METHOD OF CLEANING AN ARTHROSCOPIC SHAVER

TECHNICAL FIELD

This patent application relates to arthroscopic shavers and, more particularly, to arthroscopic shaver cleaning devices and methods for cleaning arthroscopic shavers.

BACKGROUND OF THE DISCLOSED EMBODIMENTS

Arthroscopic shavers are used to abrade and/or cut tissue or bone with a blade or burr (hereinafter collectively and individually referred to as "blade/burr") attachment in arthroscopic surgeries. The blade/burr attaches to an arthroscopic shaver handle that provides mechanical motion to the blade/burr and suction to excise tissue and bone and remove loose fragments and debris. This suction pulls the excised tissue/bone into a lumen (typically 2-4 mm in diameter) while the blade/burr oscillates and cleaves. On occasion, tissue, bone, and/or other debris becomes lodged or stuck in the blade/burr lumen. If such an event occurs, the surgical assistant may remove the blade/burr from the arthroscopic shaver handle, disassemble the blade/burr, and attempt to clear the blockage in the lumen by either using a sharp instrument (such as a spinal needle) to scoop out or clear the obstruction, or by striking the blade/burr on a hard surface within the surgical sterile field to dislodge and remove the obstruction. Such clearance methods waste the valuable time of the surgical team, require disassembly of the blade/burr components, can be dangerous, and can be damaging to the arthroscopic shaver. Further, the blade/burr must be reassembled, re-attached to the arthroscopic shaver handle, and tested to determine whether the blockage has been cleared, thereby further wasting valuable time. If the blockage has not been cleared, the process must be performed again.

Therefore, there exists a need in the art for an arthroscopic shaver cleaning device and a method of cleaning an arthroscopic shaver that reduces waste of surgical team time, eliminates disassembly of the blade/burr, and provides a more certain indication of clearance of the blockage. Further, there exists a need in the art for an arthroscopic shaver cleaning device and a method of cleaning an arthroscopic shaver that provides a sterile and safer method of clearing the blockage without risk of damage to the arthroscopic shaver.

SUMMARY OF THE DISCLOSED EMBODIMENTS

In one embodiment, a cleaning device for a blade/burr of an arthroscopic shaver is disclosed, the cleaning device comprising: a sleeve portion configured to interface with a proximal portion of the blade/burr; and a fluid connection portion operably coupled to the sleeve portion and having a fluid passageway disposed therethrough and configured to direct fluid supplied to the fluid connection portion toward the proximal portion of the blade/burr.

In another embodiment, a method of cleaning a blade/burr of an arthroscopic shaver is disclosed, the method comprising: providing an arthroscopic shaver cleaning device having a sleeve portion and a fluid connection portion; positioning a proximal portion of the blade/burr within the sleeve portion of the arthroscopic shaver cleaning device; and supplying a fluid from a fluid source through the fluid connection portion toward the proximal portion.

Other embodiments are also disclosed.

BRIEF DESCRIPTION OF THE DRAWINGS

The embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein.

DETAILED DESCRIPTION OF THE ENCLOSED EMBODIMENTS

Figure 1:
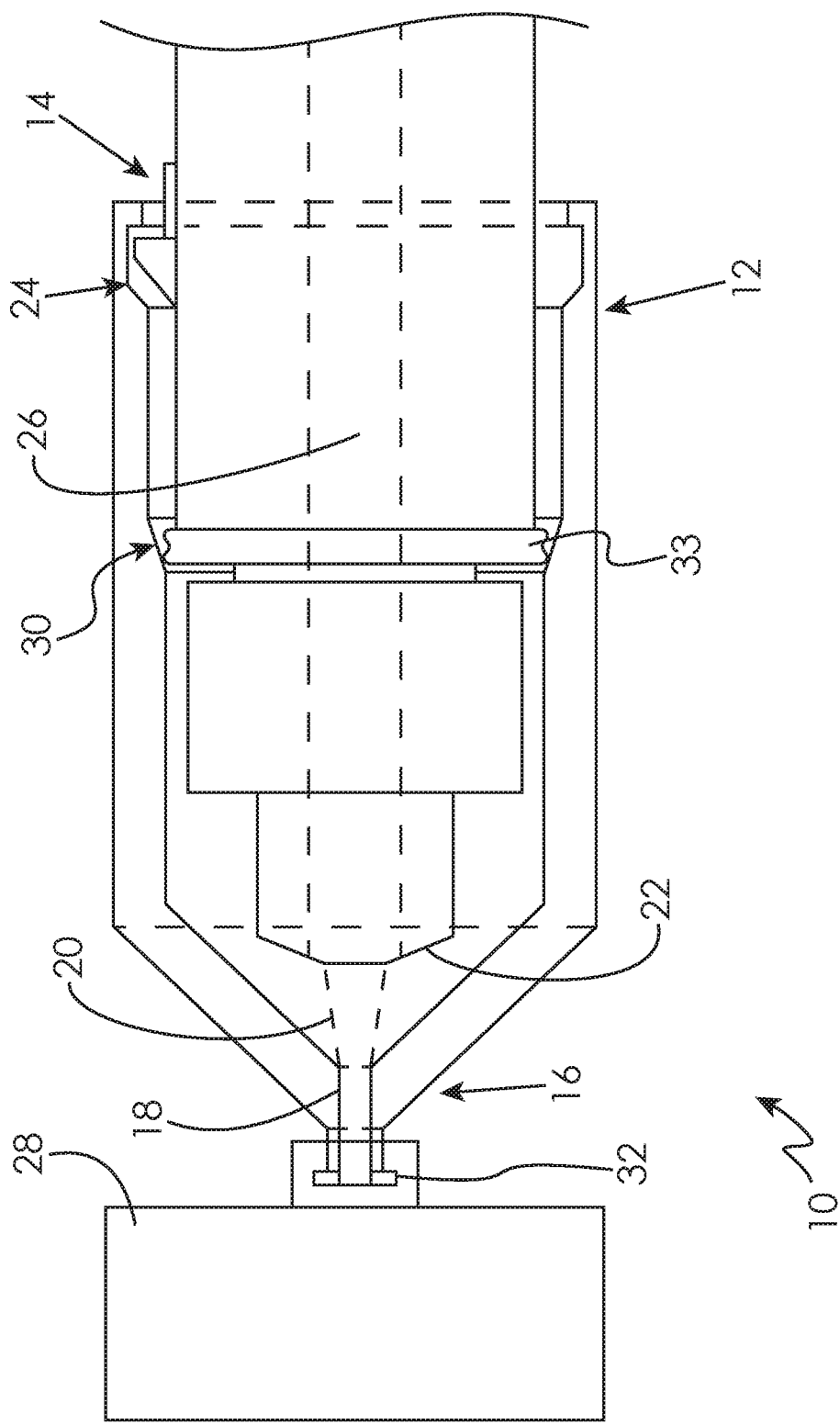
FIG. 1 is a side view of an arthroscopic shaver and an arthroscopic shaver cleaning device according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Referring now to FIG. 1, an arthroscopic shaver cleaning device 10 is illustrated in accordance with an embodiment of the present disclosure. The device 10 of FIG. 1 includes a sleeve portion 12 configured to interface with a proximal portion 14 of a blade/burr attachment of an arthroscopic shaver. The proximal portion 14 of the blade/burr is the end that is coupled to the arthroscopic shaver handle that is grasped by the surgeon, while the opposite, distal end (not shown) of the blade/burr provides the shaving functionality. The device 10 further includes a fluid connection portion 16 having a fluid passageway 18 formed therethrough and configured to direct fluid 20 toward the proximal portion 14. Although the fluid connection portion 16 is conical in the illustrated embodiment, the shape of the fluid connection portion 16 is not critical, so long as the fluid connection portion 16 is formed to allow fluid to pass therethrough. The sleeve portion 12 is shown mounted over an end 22 of the proximal portion 14 of a blade/burr.

In the illustrated embodiment, the fluid passageway 18 is configured to direct the fluid 20 toward the end 22 of the proximal portion 14 of the blade/burr. The fluid 20 may be water, saline, or any fluid operative to flush or clean a surgical instrument as described herein, including a liquid and/or gas substance. The device 10 of an embodiment includes a fluid source 28 coupled to the fluid passageway 18. In an embodiment, the fluid source 28 is configured to pressurize the fluid 20 and/or supply the pressurized fluid 20 through the fluid passageway 18 toward the proximal portion 14 of the blade/burr. In an embodiment, the pressurized fluid source 28 is or includes a syringe. In another embodiment, the pressurized fluid source is or includes a container holding a quantity of fluid under pressure. In one or more additional embodiments, the pressurized fluid source 28 is any other volume of the fluid 20 capable of being propelled through the fluid passageway 18. In an embodiment not illustrated, the fluid 20 may be supplied via a non-pressurized fluid source, such as delivering via gravity a fluid operative to dissolve debris in the proximal portion 14 without pressure, to name one non-limiting example.

In an embodiment, the fluid source 28 is configured to pressurize the fluid 20 and/or supply the pressurized fluid 20 through the fluid passageway 18 toward the proximal portion 14 and into a blade/burr lumen 26 extending from the proximal end 22 to a distal end of the blade/burr. In such embodiments, the fluid 20 flushes, dissolves, ejects, or otherwise removes debris and/or other objects from the lumen 26 and expels them from the distal end of the lumen 26. Seeing the fluid 20 freely expelled from the distal end of the lumen 26 provides visual feedback that the obstruction has been cleared.

Figure 2:
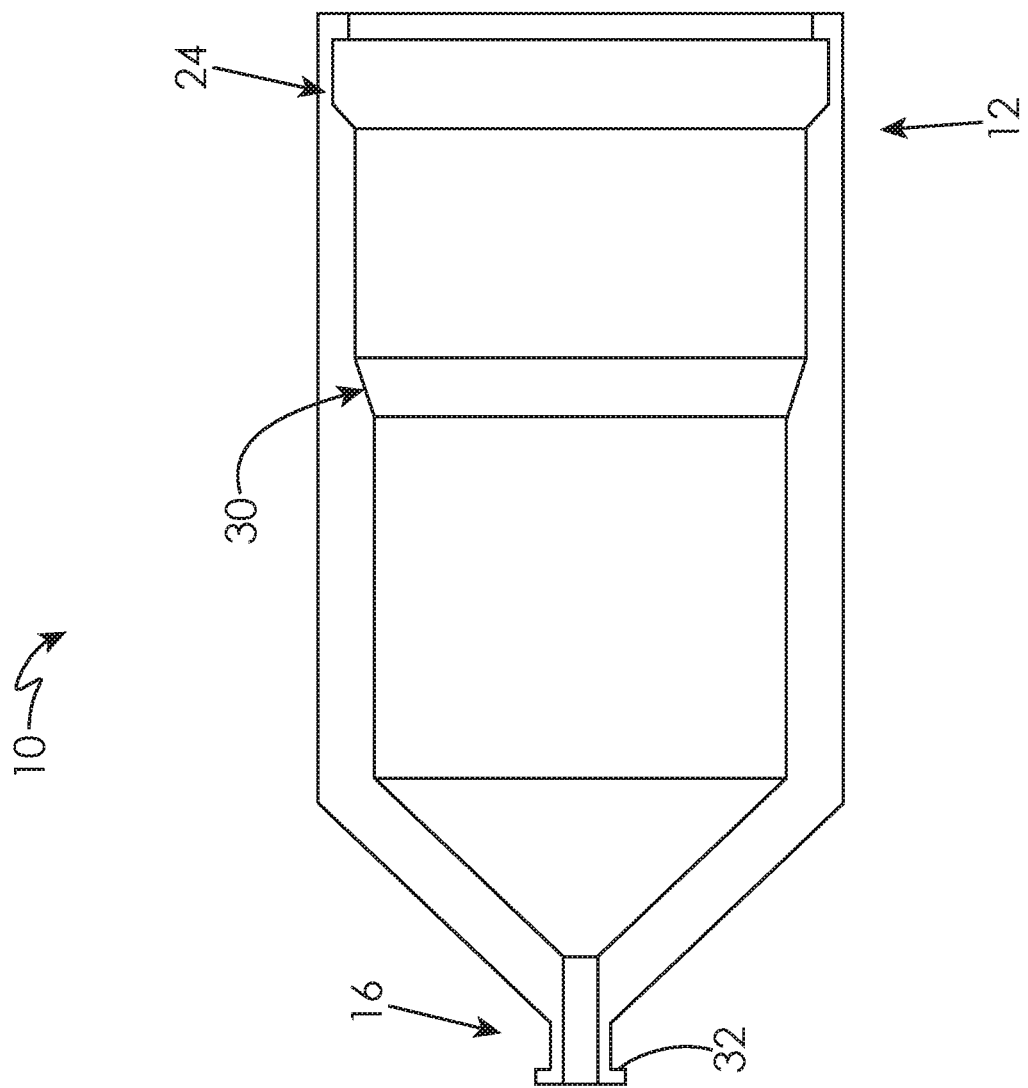
FIG. 2 is a cross-sectional view of an arthroscopic shaver cleaning device according to one embodiment of the present disclosure.

Referring now to a cross-sectional view of an embodiment of the device 10 depicted in FIG. 2, with continued reference to FIG. 1, the sleeve portion 12 of the device 10 includes a locking portion 24 configured to lock the proximal portion 14 of the blade/burr to the device 10 while in use. The device 10 of one or more embodiments further includes a sealing portion 30 disposed between the locking portion 24 and the fluid connection portion 16. The sealing portion 30, as illustrated in the embodiment of FIG. 1, is configured to contact a seal 33 located on the blade/burr, such that the fluid 20 must pass through the lumen 26 in order to exit the device 10. If the fluid cannot pass by debris lodged within the lumen 26, the seal 33 causes pressure to build up within the fluid delivered to the device 10, wherein such pressure assists in dislodging the debris from the blade/burr lumen 26.

Figure 3:
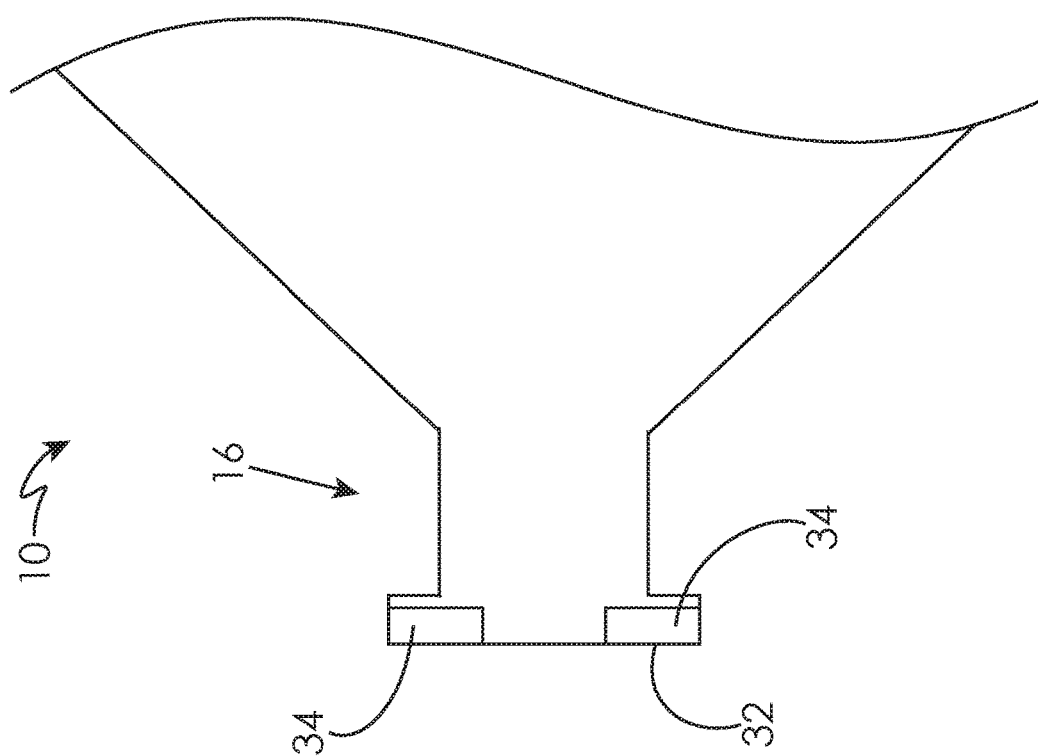
FIG. 3 is a side view of an arthroscopic shaver cleaning device according to one embodiment of the present disclosure.

In the illustrated embodiments, the fluid connection portion 16 includes a connector 32 configured to connect the fluid connection portion 16 to the pressurized fluid source 28. As best shown in the enlarged side view of the embodiment of the device 10 of FIG. 3, the connector 32 may include one or more radially-extending tab(s) 34 for connecting the fluid connection portion 16 to the pressurized fluid source 28. In the embodiment of FIG. 3, the connector 32 is a Luer-lock connector, but one or more additional connector types may be utilized with or without the tab(s) 34.

Figure 4:
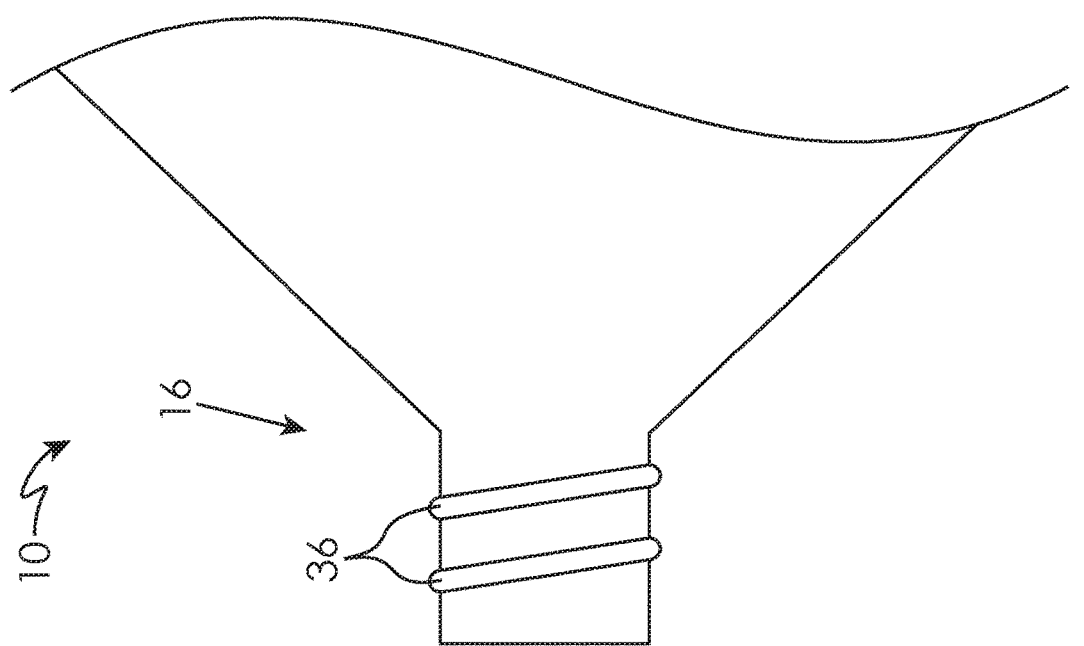
FIG. 4 is a side view of an arthroscopic shaver cleaning device according to one embodiment of the present disclosure.

Referring to FIG. 4, in another embodiment, the connector 32 includes one or more screw thread(s) (either external threads as shown or internal threads (not shown)) 36 for connecting the fluid connection portion 16 to the pressurized fluid source 28. In some embodiments, the connector 32 may also include a tapered surface or another surface or structure to enable or aid connecting the fluid connection portion 16 to the pressurized fluid source 28.

Figure 5:
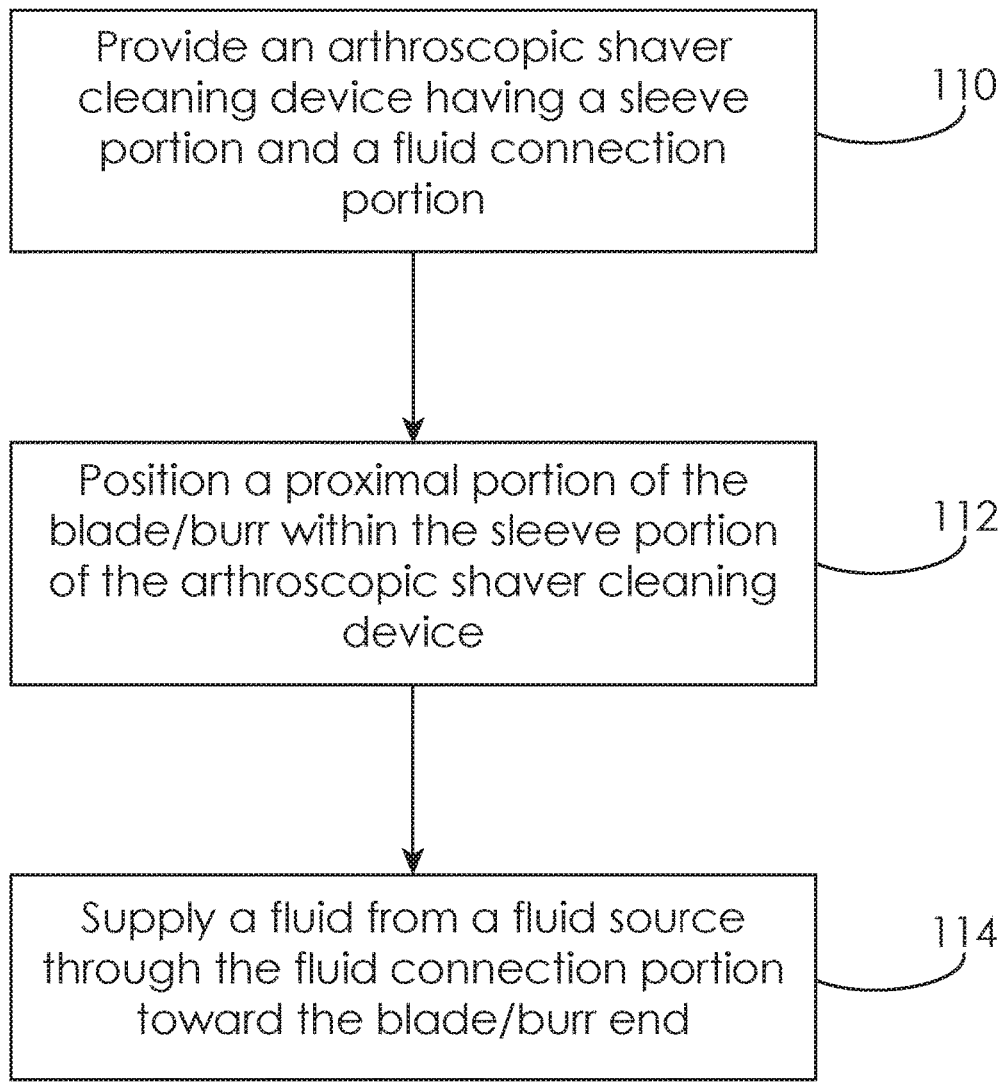
FIG. 5 illustrates a method of cleaning an arthroscopic shaver according to one embodiment of the present disclosure.

Referring now to FIG. 5, a method 100 of cleaning the lumen 26 of blade/burr is disclosed. The method 100 includes providing, at step 110, the arthroscopic shaver cleaning device 10 having the sleeve portion 12 and the fluid connection portion 16. The method 100 includes positioning, at step 112, the end 22 of the proximal portion 14 of the blade/burr within the sleeve portion 12 of the arthroscopic shaver cleaning device 10. The method 100 includes supplying, at step 114, the fluid 20 from the fluid source 28 through the fluid connection portion 16 toward the blade/burr end 22. The fluid may be used to dislodge debris within the lumen 26 so that the blade/burr is operative for further use by the surgeon.

In particular embodiments, the method 100 further includes sealing the arthroscopic shaver cleaning device 10 against the seal 33 at the sealing portion 30. The method 100 may further include pressurizing the fluid 20 from the fluid source 28 such that the fluid 20 is delivered to the proximal portion 14 under pressure. The method 100 may further include impinging upon the end 22 of the proximal portion 14 with the fluid 20. The method 100 may further include directing the fluid 20 through the end 22 of the lumen 26. The method 100 may further include connecting the sleeve portion 12 to the fluid source 28 with a connector 32 of the fluid connection portion 16.

It will be appreciated that the device 10 and method 100 embodiments disclosed herein assure clearing of tissue, bone, and other debris blockages during arthroscopic surgery. The device 10 and method 100 reduce waste of operating room time, such as by quickly providing pressurized fluid 20 to or against the end 22 of the lumen 26 and eliminating the need to disassemble the blade/burr. In a non-limiting example, the device 10 including a syringe to supply pressurized fluid 20 may be easily stored, retrieved, and deployed within the surgical sterile field in the event of a blockage during use of the arthroscopic shaver. Further, the device 10 and method 100 embodiments disclosed herein maintain the sterile environment of the operating room while the fluid 20 safely flushes the lumen 26 and clears the blockage without risk of damage to the blade/burr.

While the disclosure has been illustrated and described in detail in the drawings and foregoing description, the same is to be considered as illustrative and not restrictive in character, it being understood that only certain embodiments have been shown and described and that all changes and modifications that come within the spirit of the disclosure are desired to be protected.

What is claimed is:

1. A method of cleaning a blade/burr of an arthroscopic shaver, for use in operating on a patient, while the blade/burr remains sterile within a surgical sterile field during arthroscopic surgery, the method comprising:
   providing, within the surgical sterile field, an arthroscopic shaver cleaning device having a sleeve portion and a fluid connection portion;
   positioning, within the surgical sterile field and with the blade/burr exterior to the patient, a proximal portion of the blade/burr within the sleeve portion of the arthroscopic shaver cleaning device; and
   supplying, within the surgical sterile field, a fluid from a fluid source through the fluid connection portion toward the proximal portion;
   wherein the fluid flows from the proximal portion of the blade/burr to a distal portion of the blade/burr at a pressure sufficient to clear a blockage within the blade/burr; and
   wherein visual observation of the expulsion of the blockage and the fluid from the distal end of the blade/burr provides visual feedback that the blockage has been cleared.

2. The method of claim 1, further comprising sealing the arthroscopic shaver cleaning device against the proximal portion of the blade/burr at the sleeve portion.

3. The method of claim 1, wherein the step of supplying a fluid comprises supplying a fluid under pressure.

4. The method of claim 1, further comprising impinging the fluid upon the proximal portion.

5. The method of claim 1, further comprising directing the fluid through a lumen formed in the proximal portion of the blade/burr.

6. The method of claim 1, further comprising connecting the sleeve portion to the fluid source with a connector of the fluid connection portion.

7. A method of cleaning a blade/burr of an arthroscopic shaver, for use in operating on a patient, while the blade/burr remains sterile within a surgical sterile field during arthroscopic surgery, the method comprising:
   providing, within the surgical sterile field, an arthroscopic shaver cleaning device having a sleeve portion and a fluid connection portion;
   positioning, within the surgical sterile field and with the blade/burr exterior to the patient, a proximal portion of the blade/burr within the sleeve portion of the arthroscopic shaver cleaning device; and
   supplying, within the surgical sterile field, a fluid from a fluid source through the fluid connection portion toward the proximal portion;
   wherein the fluid flows from the proximal portion of the blade/burr to a distal portion of the blade/burr at a pressure sufficient to clear a blockage within the blade/burr.

8. The method of claim 7, further comprising sealing the arthroscopic shaver cleaning device against the proximal portion of the blade/burr at the sleeve portion.

9. The method of claim 7, wherein the step of supplying a fluid comprises supplying a fluid under pressure.

10. The method of claim 7, further comprising impinging the fluid upon the proximal portion.

11. The method of claim 7, further comprising directing the fluid through a lumen formed in the proximal portion of the blade/burr.

12. The method of claim 7, further comprising connecting the sleeve portion to the fluid source with a connector of the fluid connection portion.

* * * * *